United States Patent
Hasegawa et al.

(10) Patent No.: US 10,864,053 B2
(45) Date of Patent: Dec. 15, 2020

(54) FLEXIBLE MANIPULATOR

(71) Applicant: OLYMPUS CORPORATION, Tokyo (JP)

(72) Inventors: Mitsuaki Hasegawa, Tokyo (JP); Ryoji Hyodo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 182 days.

(21) Appl. No.: 16/145,258

(22) Filed: Sep. 28, 2018

(65) Prior Publication Data

US 2019/0029767 A1 Jan. 31, 2019

Related U.S. Application Data

(63) Continuation of application No. PCT/JP2016/061518, filed on Apr. 8, 2016.

(51) Int. Cl.
*A61B 34/00* (2016.01)
*A61B 34/30* (2016.01)
(Continued)

(52) U.S. Cl.
CPC ............ *A61B 34/71* (2016.02); *A61B 34/30* (2016.02); *A61B 17/29* (2013.01);
(Continued)

(58) Field of Classification Search
CPC ........ A61B 2090/061; A61B 2034/715; A61B 2034/301; A61B 2017/2929; A61B 2017/2905; A61B 2017/2903; A61B 17/29; A61B 2017/00327; A61B 34/71; A61B 34/30
See application file for complete search history.

(56) References Cited

U.S. PATENT DOCUMENTS 5,842,381 A 12/1998 Felten
2002/0198542 A1 12/2002 Yamamoto et al.
(Continued)

FOREIGN PATENT DOCUMENTS

EP 2777561 A1 9/2014
EP 3085324 A1 10/2016
(Continued)

OTHER PUBLICATIONS

Japanese Office Action dated Aug. 13, 2019 in Japanese Patent Application No. 2018-510203.
(Continued)

*Primary Examiner* — George J Ulsh
(74) *Attorney, Agent, or Firm* — Scully, Scott, Murphy & Presser, P.C.

(57) ABSTRACT

A medical manipulator includes: an elongated flexible portion configured to be inserted into a body; an end effector disposed on a distal end of the elongated flexible portion; a proximal portion coupled to a proximal end of the elongated flexible portion, the proximal portion being configured to generate power for actuating the end effector; at least two wires configured to transmit the power to the end effector; at least two sheaths configured to form a path of each of the wires within the elongated flexible portion; and a rotating mechanism configured such that either a distal end or a proximal end of each of the sheaths rotates relative to the elongated flexible portion about a longitudinal axis of the elongated flexible portion.

15 Claims, 4 Drawing Sheets

(51) Int. Cl.
  *A61B 17/29*    (2006.01)
  *A61B 90/00*    (2016.01)
  *A61B 17/00*    (2006.01)

(52) U.S. Cl.
  CPC ............ *A61B 2017/00327* (2013.01); *A61B 2017/2903* (2013.01); *A61B 2017/2905* (2013.01); *A61B 2017/2929* (2013.01); *A61B 2034/301* (2016.02); *A61B 2034/715* (2016.02); *A61B 2090/061* (2016.02)

(56) References Cited

U.S. PATENT DOCUMENTS

| | | |
|---|---|---|
| 2003/0135204 A1 | 7/2003 | Lee et al. |
| 2004/0019352 A1 | 1/2004 | Kidooka |
| 2004/0193146 A1 | 9/2004 | Lee et al. |
| 2011/0196419 A1 | 8/2011 | Cooper |
| 2012/0123441 A1 | 5/2012 | Au et al. |
| 2014/0277107 A1 | 9/2014 | Ishida et al. |
| 2015/0289942 A1 | 10/2015 | Au et al. |
| 2016/0256183 A1 | 9/2016 | Cooper |
| 2016/0287346 A1 | 10/2016 | Hyodo et al. |
| 2016/0316996 A1 | 11/2016 | Nakayama et al. |
| 2017/0304014 A1 | 10/2017 | Au et al. |

FOREIGN PATENT DOCUMENTS

| | | |
|---|---|---|
| EP | 3 095 375 A1 | 11/2016 |
| EP | 3181069 A1 | 6/2017 |
| JP | H10-504765 A | 5/1998 |
| JP | 2003-038495 A | 2/2003 |
| JP | 2009-142513 A | 7/2009 |
| JP | 4420593 B2 | 2/2010 |
| JP | 2010-221329 A | 10/2010 |
| JP | 2012-217588 A | 11/2012 |
| JP | 2013-518665 A | 5/2013 |
| JP | 2014-504897 A | 2/2014 |
| JP | 2014-176483 A | 9/2014 |
| JP | 2015-131015 A | 7/2015 |
| WO | WO 2011/097095 A1 | 8/2011 |
| WO | WO 2012/064528 A1 | 5/2012 |
| WO | WO 2015/093602 A1 | 6/2015 |

OTHER PUBLICATIONS

International Search Report dated Jul. 5, 2016 issued in PCT/JP2016/061518.

FLEXIBLE MANIPULATOR

CROSS-REFERENCE TO RELATED APPLICATIONS

This is a continuation of International Application PCT/JP2016/061518 which is hereby incorporated by reference herein in its entirety.

TECHNICAL FIELD

The present invention relates to a flexible manipulator.

BACKGROUND ART

In the case where two lumens that respectively guide two wires for driving a movable unit are formed inside a flexible insertion portion so as to extend straight in the longitudinal direction of the insertion unit, bending the insertion unit generates a difference in path length between the two wires. If one of the wires is stretched while the other is loosened, the movable unit moves in an unintended direction. In order to avoid this issue, a flexible manipulator having two or more lumens spirally twisted about the longitudinal axis of the insertion unit has been proposed (for example, refer to PTL 1).

According to PTL 1, adjusting the twist pitch of the spiral lumens within a particular range can reduce the difference in path length and can suppress movement of the movable unit in an unintended direction.

CITATION LIST

Patent Literature

{PTL 1} WO 2015/093602

SUMMARY OF INVENTION

According to one aspect, the present invention provides a medical manipulator including an elongated flexible portion configured to be inserted into a body; an end effector disposed on a distal end of the elongated flexible portion; a proximal portion coupled to a proximal end of the elongated flexible portion, the proximal portion being configured to generate power for actuating the end effector; at least two wires configured to transmit the power to the end effector; at least two sheaths configured to form a path of each of the wires within the elongated flexible portion; and a rotating mechanism configured such that either a distal end or a proximal end of each of the sheaths rotates relative to the elongated flexible portion about a longitudinal axis of the elongated flexible portion.

DESCRIPTION OF EMBODIMENTS

A flexible manipulator 1 according to one embodiment of the present invention will now be described with reference to the drawings.

Figure 1:
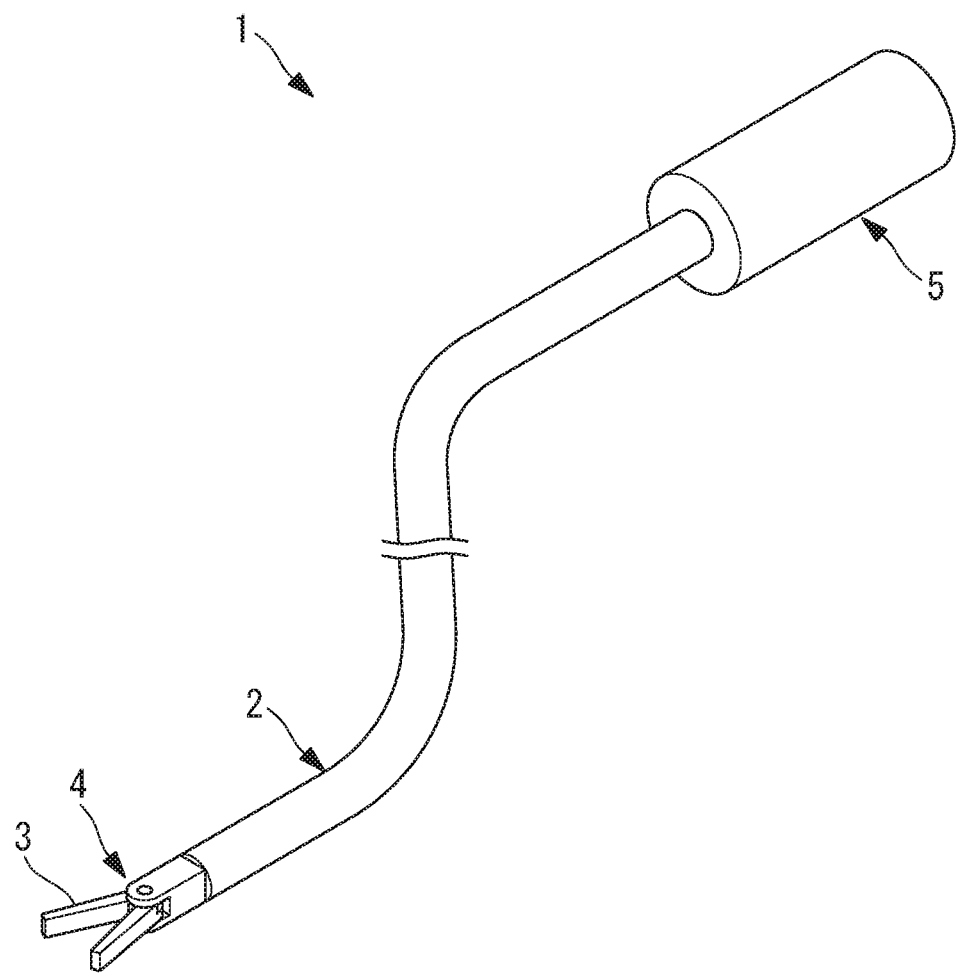
FIG. 1 is a diagram illustrating the overall structure of a flexible manipulator according to one embodiment of the present invention.
Figure 2:
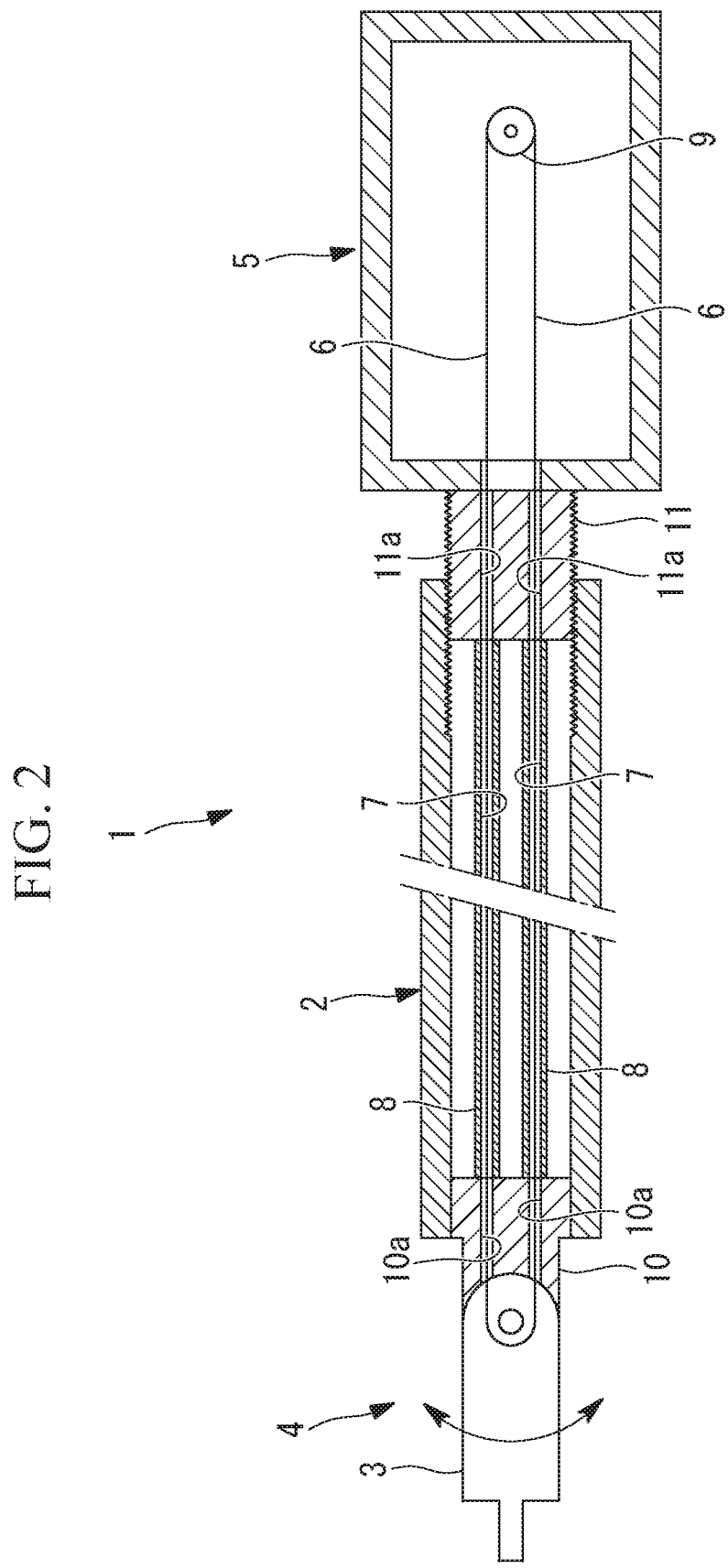
FIG. 2 is a vertical sectional view of the flexible manipulator illustrated in FIG. 1.

As illustrated in FIGS. 1 and 2, the flexible manipulator 1 of this embodiment includes, for example, an insertion unit 2, a movable unit 4, a drive unit 5, wires (drive-force-transmitting members) 6, and sheaths (path-forming members or tubular members) 8. The insertion unit 2 is inserted into the interior of a body cavity of a patient through a forceps channel of an endoscope to be inserted into the body cavity of the patient. The movable unit 4 has a joint and a treatment unit 3 such as grasping forceps disposed at a distal end of the insertion unit 2. The drive unit 5 is disposed at a proximal end of the insertion unit 2 and actuates the movable unit 4. The wires 6 transmit the drive force generated in the drive unit 5 to the movable unit 4. Each of the sheaths 8 has an inner hole 7 that forms a path, through which the wire 6 passes from the proximal end to the distal end of the insertion unit 2.

The insertion unit 2 is configured as a flexible tube in which some portions or the entirety thereof in the length direction can be bent.

The drive unit 5 includes a pulley 9 connected to a motor, which is not illustrated in the drawing. The wires 6 are looped over the pulley 9.

In the example illustrated in FIG. 2, to simplify the description, there are two wires 6 in the insertion unit 2.

When the pulley 9 is rotated by the rotative force from the motor, the tension on the wire 6 on one side of the pulley 9 is increased, and the tension on the wire 6 on the other side of the pulley 9 is decreased. The difference in tension between the two wires 6 serves as a drive force and is transmitted to the movable unit 4 at the distal end of the insertion unit 2 so that the joint of the movable unit 4 can pivot.

As illustrated in FIG. 2, each of the sheaths 8 is formed as a tube having a single inner hole 7 through which one of the two wires 6 passes.

The two sheaths 8 are respectively located at positions an equal distance away in radial directions relative to the center axis of the insertion unit 2. The distal ends of the sheaths 8 are fixed to a distal end member 10, which fixes the movable unit 4 to the distal end of the insertion unit 2. The proximal ends of the sheaths 8 are fixed to a proximal end member 11, which is attached to the proximal end of the insertion unit 2 by screwing so as to be rotatable about the center axis of the insertion unit 2. The distal end member 10 and the proximal end member 11 have through holes 10a and 11a, through which the wires 6 pass.

The drive unit 5 is fixed to the proximal end member 11. The two wires 6 looped over the pulley 9 of the drive unit 5 respectively pass through the through holes 11a in the proximal end member 11 so that the wires 6 pass through the interiors of different sheaths 8. The wires 6 pass through the through holes 10a in the distal end member 10 and are connected to the movable unit 4.

Figure 3:
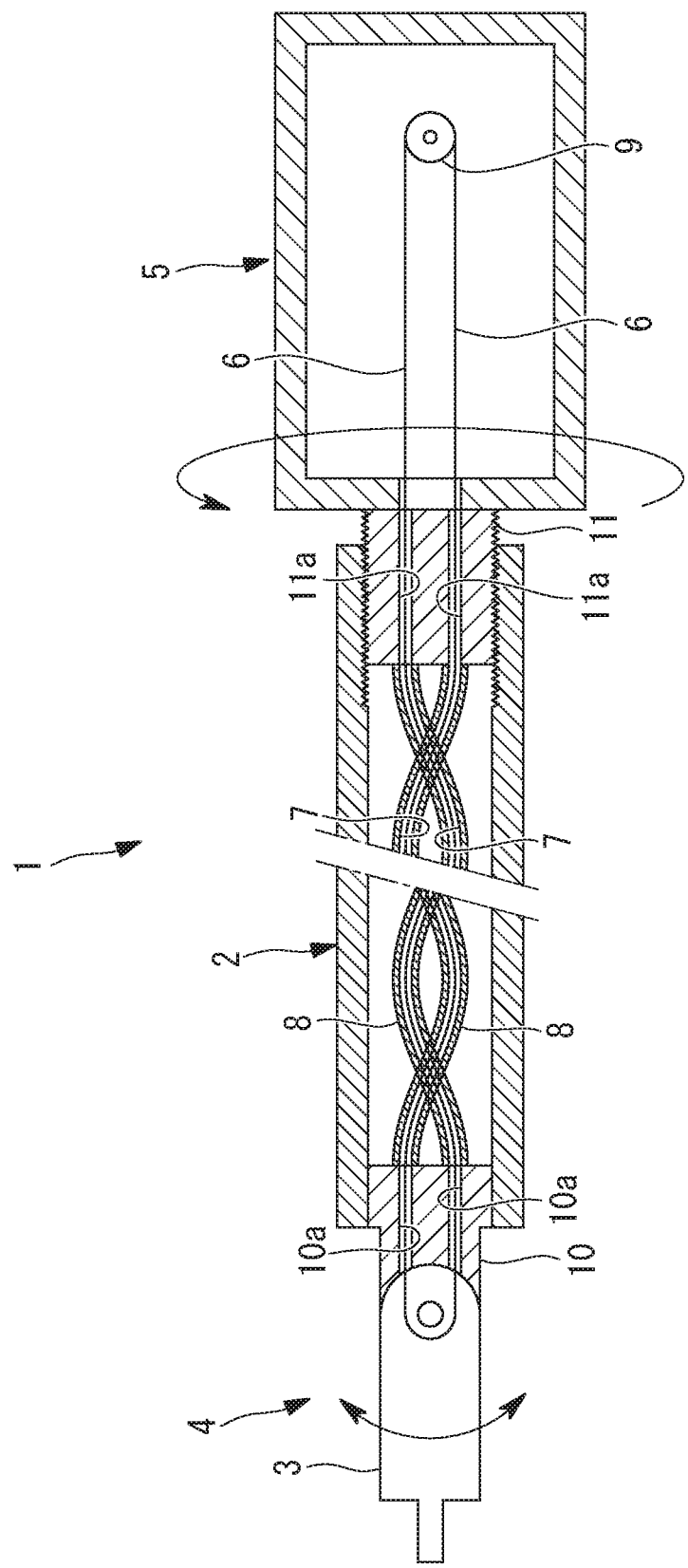
FIG. 3 is a vertical sectional view illustrating a state in which sheaths of the flexible manipulator illustrated in FIG. 2 are twisted.

Thus, when the drive unit 5 and the proximal end member 11 are rotated about the longitudinal axis of the insertion unit 2 relative to the insertion unit 2, the proximal end side of the sheaths 8 undergoes relative rotation about the longitudinal axis of the insertion unit 2 relative to the distal end side of the sheaths 8. As a result, as illustrated in FIG. 3, the two sheaths 8 are twisted into a spiral about the longitudinal axis of the insertion unit 2.

The operation of the flexible manipulator 1 of this embodiment, configured as such, will now be described.

The treatment is performed in the body cavity of a patient by using the flexible manipulator 1 of this embodiment as follows. The shape of an endoscope inserted into the body cavity of the patient is detected in advance by, for example, inserting an optical fiber sensor into the forceps channel, and the bend length of the insertion unit 2 that would be bent when the flexible manipulator 1 is inserted into the forceps channel is estimated.

Next, the rotation angle θ is calculated by equation (1) below from the estimated bend length L1 and the total length L2 of the insertion unit 2:

$$\theta = 360° \times L2/L1 \quad (1)$$

Then, the drive unit 5 is rotated by the calculated angle θ about the center axis of the insertion unit 2 relative to the insertion unit 2. In this manner, since the proximal end member 11 and the distal end member 10 are rotated relative to each other about the center axis of the insertion unit 2, the two sheaths 8, the two ends of which are respectively fixed to the proximal end member 11 and the distal end member 10, are twisted about the center axis of the insertion unit 2 so as to form a spiral.

Here, since the angle of rotation is the angle θ calculated by equation (1), the pitch of the sheaths 8 forming a spiral is set to be equal to the bend length. In other words, since the two sheaths 8 are twisted into a spiral having a pitch equal to the bend length, the lengths of the two sheaths 8 that lie at the bend portion of the insertion unit 2, namely, the two path lengths formed by the two sheaths 8 in the inner holes 7, can be equal to each other irrespective of the extent of the bending.

Thus, generation of a difference in path length due to bending of the insertion unit 2 can be prevented, and generation of a difference in tension between the wires 6, which pass through the sheaths 8, due to bending of the insertion unit 2 can be prevented.

As described above, according to the flexible manipulator 1 of this embodiment, generation of a difference in path length due to bending of the insertion unit 2 is prevented, and, thus, there is an advantages in that the movable unit 4 is prevented from moving in an unexpected direction.

The pitch of the spiral shape of the sheaths 8 may be set so that an integral multiple of the pitch is equal to the bend length of the insertion unit 2. In this manner, the same effects as those described above can be exhibited. However, when the pitch is equal to the bend length, the friction between the inner surfaces of the inner holes 7 in the sheaths 8 and the wires 6 can be minimized, and thus degradation of the controllability of the movable unit 4 can be prevented.

Moreover, according to this embodiment, as illustrated in FIGS. 2 and 3, the proximal end member 11 and the insertion unit 2 are connected to each other by screwing. Thus, when the proximal end member 11 is rotated to twist the sheaths 8 into a spiral, the proximal end member 11 can be moved toward the distal end in the longitudinal axis direction of the insertion unit 2 according to the screw pitch. Although the sheaths 8 become shorter in the longitudinal direction of the insertion unit 2 when twisted into a spiral, the proximal end member 11 moves toward the distal end, and thus, an increase in the tension acting on the sheaths 8 can be prevented.

Figure 4:
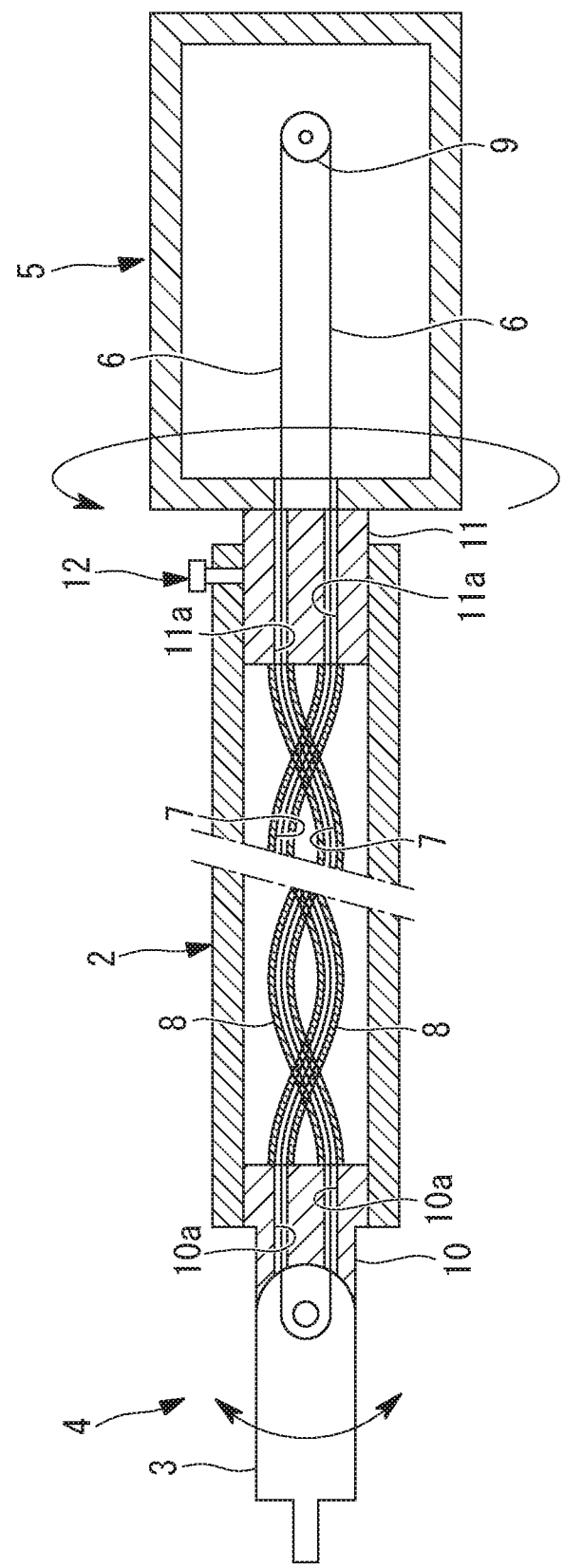
FIG. 4 is a vertical sectional view of a modification of the flexible manipulator illustrated in FIG. 1.

Alternatively, a cam may be employed instead of the screw, or, as illustrated in FIG. 4, fitting may be achieved by forming simple cylindrical surfaces that enable movement in the longitudinal direction. Moreover, in this case, a lock unit 12 that maintains the proximal end member 11, which has been rotated about the center axis relative to the insertion unit 2, at the position at the arbitrary rotation angle is preferably provided.

The lock unit 12 may be a chucking mechanism (not illustrated) that chucks the proximal end member 11 in the radial direction to lock the proximal end member 11 or, as illustrated in FIG. 4, a pushing screw or the like that pushes the proximal end member 11 in the radial direction.

In this embodiment, an example in which two sheaths 8 into which two wires 6 are respectively inserted serve as path-forming members is described. Alternatively, a multi-lumen tube that can be twisted about the center axis and has two or more inner holes 7, into each of which one wire 6 is inserted, may be employed.

Although two sheaths 8 are described as an example, three or more sheaths 8 may be provided. Furthermore, two or more space-keeping members may be installed with spaces between one another in the longitudinal direction of the insertion unit 2 so that the sheaths 8 disposed at the respective positions in the insertion unit stay at the same radial positions in the insertion unit 2.

Although the shape of the forceps channel of the endoscope inserted into the body cavity is measured so as to estimate the bend shape of the flexible manipulator 1 in this embodiment, the bend shape may instead be estimated from the shape of the body cavity measured by using a CT image or the like acquired for the surgery. Alternatively, a database of the bend shapes of the insertion unit 2 for delivering the movable unit 4 of the flexible manipulator 1 to the target site may be prepared in advance in association with treatment target sites, and the bend shape may be read out from the database by inputting the target site.

Although an example in which the drive unit 5 is rotated relative to the insertion unit 2 prior to the insertion into the body is described, the drive unit 5 may be rotated after the insertion.

The above-described embodiment also leads to the following invention.

According to one aspect, the present invention provides a flexible manipulator including an elongated flexible tubular insertion unit; a movable unit disposed at a distal end of the insertion unit; a drive unit disposed at a proximal end of the insertion unit; two or more elongated drive force-transmitting members that transmit power generated in the drive unit to the movable unit; and a flexible path-forming member that forms, inside the insertion unit, two or more paths through which the drive force-transmitting members pass in a longitudinal direction, the two or more paths being formed on a radially outer side relative to a center axis of the insertion unit. The path-forming member has two ends respectively disposed at the distal end and the proximal end of the insertion unit, and the two ends are rotatable relative to each other about the center axis of the insertion unit.

According to this aspect, when the drive unit disposed at the proximal end of the insertion unit is actuated, power generated in the drive unit is transmitted to the movable unit at the distal end of the insertion unit through the drive-force-transmitting members passing through the paths formed by the path-forming member, and the movable unit is actuated thereby. When the elongated flexible insertion portion is bent, the shape of the paths, through which the drive-force-transmitting members pass, inside the path-forming member changes with the bending.

In this case, since the bend shape of the insertion unit is determined by, for example, the shape of the insertion-receiving part, for example, the body cavity of the patient leading up to the target organ, the bend length is not constant. To address this issue, according to this aspect, two or more paths formed by the path-forming member can be twisted about the center axis of the insertion unit into a spiral by rotating the two ends of the path-forming member relative to each other about the center axis of the insertion unit, and the spiral pitch can be set at a arbitrary pitch by adjusting the relative rotation angle.

In other words, even when the bend length of the insertion unit is changed, the spiral pitch can be set to a maximum pitch that minimizes the difference in path length by adjusting the relative rotation angle of the two ends of the path-forming member. As a result, generation of a difference in path length between two or more drive-force-transmitting members can be suppressed for any bend length of the insertion unit, and the friction acting on the drive-force-transmitting members is reduced so that degradation of the controllability of the movable unit can be prevented.

In the aspect described above, the path-forming member may include a plurality of tubular members each having a single inner hole, through which one of the drive force-transmitting members passes.

In this manner, when the two ends of the path-forming member are rotated relative to each other about the center axis of the insertion unit, the tubular members are twisted into a spiral about the center axis of the insertion unit, and thus the inner holes of the tubular members can form, inside the insertion unit, two or more paths having a spiral shape with a desired pitch.

In the aspect described above, the path-forming member may include a tubular member having a plurality of inner holes, through which the drive force-transmitting members pass.

In this manner, when the two ends of the path-forming member are rotated relative to each other about the center axis of the insertion unit, the tubular member is twisted about the center axis of the insertion unit, and thus the inner holes in the tubular member can form, inside the insertion unit, two or more paths having a spiral shape with a desired pitch about the center axis of the insertion unit.

In the aspect described above, a distal end of the path-forming member may be fixed between the movable unit and the distal end of the insertion unit, and a proximal end of the path-forming member may be fixed to the drive unit.

In this manner, when the insertion unit and the drive unit are rotated relative to each other about the center axis of the insertion unit, the drive unit and the proximal end of the path-forming member can be rotated together, and a spiral path twisted at a desired pitch can be formed in the insertion unit.

In the aspect described above, the flexible manipulator may further include a lock unit that can lock, at an arbitrary rotation angle position, relative rotation between the insertion unit and the drive unit about the center axis.

In this manner, after the lock effected by the lock unit is released and the two ends of the path-forming member are rotated relative to each other by a desired rotation angle about the center axis of the insertion unit, a spiral path having a desired pitch can be maintained by actuating the lock unit to lock the insertion unit and the drive unit.

REFERENCE SIGNS LIST 1 flexible manipulator
2 insertion unit
4 movable unit
5 drive unit
6 wire (drive force-transmitting member)
7 inner hole
8 sheath (path-forming member or tubular member)
12 fixing portion

The invention claimed is:
1. A medical manipulator comprising:
an elongated flexible tube configured to be inserted into a body;
an end effector disposed on a distal end of the elongated flexible tube;
a proximal portion coupled to a proximal end of the elongated flexible tube, the proximal portion being configured to generate power for actuating the end effector;
at least two wires configured to transmit the power to the end effector;
at least two sheaths configured to form a path for each of the at least two wires within the elongated flexible tube; and
a rotating mechanism configured such that either a distal end or a proximal end of each of the sheaths rotates relative to the elongated flexible tube about a longitudinal axis of the elongated flexible tube,
wherein the rotating mechanism comprises:
a distal end member coupled to the distal end of each of the at least two sheaths, the distal end member being configured to be fixed to the elongated flexible tube;
a rotating member coupled to the proximal end of each of the at least two sheaths and the proximal portion, the rotating member being configured to rotate relative to the elongated flexible tube about the longitudinal axis of the elongated flexible tube.

2. The medical manipulator according to claim 1, wherein the rotating mechanism further comprises a lock configured to lock at an arbitrary position of between the rotating member and the elongated flexible tube.

3. The medical manipulator according to claim 1, wherein the rotating member and an inner wall of the elongated flexible tube are rotatably connected to each other in the form of a screw.

4. The medical manipulator according to claim 1, wherein the rotating mechanism is configured such that the path for each of the at least two wires is a spiral of an arbitrary pitch.

5. A manipulator comprising:
an elongated insertion unit;
a movable unit disposed at a distal end of the insertion unit;
a drive unit means for generating power to actuate the movable unit, the drive unit means being disposed at a proximal end of the insertion unit;
two or more elongated drive-force-transmitting members means for transmitting the power;
a flexible path-forming member means for forming, inside the insertion unit, two or more paths through which the two or more drive force-transmitting members means pass in a longitudinal direction, the two or more paths being formed on a radially outer side relative to a center axis of the insertion unit, a distal end of the path-forming member means being configured to be fixed to the insertion unit, and
a proximal end of the path-forming member means being rotatable relative to the insertion unit about the center axis; and
a rotating portion coupled to the proximal end of the path-forming member means and the drive unit means, the rotating portion being configured to rotate relative to the insertion unit about the center axis.

6. The flexible manipulator according to claim 5, wherein the path-forming member means comprises a plurality of tubular members each having a single inner hole, through which one of the two or more drive force-transmitting members means passes.

7. The flexible manipulator according to claim 5, wherein the path-forming member means comprises a tubular member having a plurality of inner holes, through which the two or more drive force-transmitting members means pass.

8. The flexible manipulator according to claim 5, wherein a distal end of the path-forming member means is fixed between the movable unit and the insertion unit, and a proximal end of the path-forming member means is fixed to the drive unit means.

9. The flexible manipulator according to claim 8, further comprising a lock unit means for locking, at an arbitrary rotation angle position, relative rotation between the insertion unit and the drive unit means about the center axis.

10. The flexible manipulator according to claim 5, wherein the rotating portion is configured such that the proximal end of the path-forming member means rotates relative to the insertion unit about the center axis.

11. A medical manipulator comprising:
an elongated flexible tube configured to be inserted into a body;
an end effector disposed on a distal end of the elongated flexible tube;
a proximal portion coupled to a proximal end of the elongated flexible tube, the proximal portion being configured to generate power for actuating the end effector;
at least two wires configured to transmit the power to the end effector;
at least two sheaths configured to form a path for each of the at least two wires within the elongated flexible tube; and
a rotating member coupled to a proximal end of each of the at least two sheaths and the proximal portion, the rotating member being configured to rotate relative to the elongated flexible tube about a longitudinal axis of the elongated flexible tube.

12. The medical manipulator according to claim 11, wherein the rotating member is configured such that the proximal end of each of the at least two sheaths rotates relative to the elongated flexible tube about a longitudinal axis of the elongated flexible tube.

13. The medical manipulator according to claim 11, further comprising a lock configured to lock at an arbitrary position of between the rotating member and the elongated flexible tube.

14. The medical manipulator according to claim 11, wherein the rotating member and an inner wall of the elongated flexible tube are rotatably connected to each other in the form of a screw.

15. The medical manipulator according to claim 11, wherein the path for each of the at least two wires is a spiral of an arbitrary pitch.

* * * * *